United States Patent [19]

Haast

[11] Patent Number: 4,741,902

[45] Date of Patent: May 3, 1988

[54] COMPOSITIONS FOR TREATMENT OF NEUROLOGICAL AND RELATED DISORDERS

[76] Inventor: William E. Haast, Miami Serpentarium Laboratories, Innovation Center, University of Utah Research Park, 419 Wakara Way, Salt Lake City, Utah 84108

[21] Appl. No.: 885,091

[22] Filed: Jul. 14, 1986

[51] Int. Cl.$^4$ .................... A61K 39/00; A61K 35/58
[52] U.S. Cl. ........................................ 424/88; 424/98; 514/825; 514/885; 514/903; 514/907
[58] Field of Search .................. 424/88, 98; 514/825, 514/885, 903, 907

[56] References Cited

U.S. PATENT DOCUMENTS 4,126,676  11/1978  Sanders ................................ 424/98
4,341,762   7/1982  Haast .................................... 424/88

Primary Examiner—J. R. Brown
Assistant Examiner—John W. Rollins
Attorney, Agent, or Firm—Kenneth E. Darnell

[57] ABSTRACT

The invention provides compositions of matter having pharmacological activity and which are useful in the treatment of the symptoms of neurological and other disorders, particularly those disorders which are caused by malfunction of the immune mechanism. The present compositions include venoms and/or venom fractions extracted from various elapid and viperid snakes and generally include a postsynaptic component capable of binding to nicotinic acetylcholine receptors of cells, a presynaptic component capable of inhibition of acetylcholine release, and a viperid component stimulative of the immune system. According to the present invention, the viperid component of the present compositions of matter preferably constitutes a venom fraction which is absent certain enzymes such as L-amino acid oxidase and phosphodiesterase, these compositions being of particular utility due to the absence of a hemorrhagic effect when used in the treatment of mammals. Methods of preparation and use of the present compositions of matter are also disclosed.

12 Claims, No Drawings

COMPOSITIONS FOR TREATMENT OF NEUROLOGICAL AND RELATED DISORDERS

BACKGROUND OF THE INVENTION

1. Field of the Invention

The invention relates generally to pharmacologically active compositions of matter comprised of snake venoms and/or snake venom fractions administered in disease mitigating quantities into the systemic circulation of mammals and particularly relates to the use of such compositions of matter for treatment of the symptomology of progressive degenerative neurological disorders, such as multiple sclerosis, amyotropic lateral sclerosis, and of the disease complex generally referred to as arthritis, particularly rheumatoid arthritis.

2. Description of the Prior Art

Various compositions of matter derived from snake venoms have previously been proposed for use in the treatment of neurological disease. In U.S. Pat. No. 4,126,676 to Sanders, neurological diseases such as amyotropic lateral sclerosis were proposed for treatment by the administration of a detoxified snake venom neurotoxin derived from the venom of the Naja genus. In U.S. Pat. No. 4,341,762 to the present inventor, compositions of matter including venoms and/or venom fractions extracted from various elapid and viperid snakes were disclosed as having pharmacological activity and having use in the treatment of the symptomology of neurological and other disorders, particularly disorders caused by malfunction of immune mechanisms. In this patent, administration in disease mitigating quantities of pharmacologically active compositions of matter comprised of snake venoms and/or snake venom fractions into the systemic circulation by subcutaneous, intramuscular or intravenous injections is described in detail for treatment of the symptomology of progressive degenerative neurological disorders, such as multiple sclerosis and amyotropic lateral sclerosis, and of the disease complex generally referred to as arthritis, particularly rheumatoid arthritis. The compositions of matter disclosed in U.S. Pat. No. 4,341,762 are also used to treat viral and autoimmune disorders by stimulation of the immune mechanisms of the body. These compositions preferably contain a neurotoxin having postsynaptic activity and which binds strongly to receptor sites of cells, and wherein reversibility of the binding is preferred. Suitable postsynaptic neurotoxins according to U.S. Pat. No. 4,341,762 are found in reptile venoms of the family Elapidae, subfamily Elapinae, and particularly the genera Naja, Ophiophagus, Dendroaspis, and others. The well-known "long" postsynaptic neurotoxin, known as α-toxin or as cobratoxin, of Naja naja siamensis (kaouthia) is particularly suited as the postsynaptic neurotoxin or receptor site "blocking agent" described in U.S. Pat. No. 4,341,762.

The compositions of matter of U.S. Pat. No. 4,341,762 also preferably include a presynaptic neurotoxin which typically inhibits the release of acetylcholine and is generally regarded as having "phospholipase activity",. the presynaptic neurotoxins of choice also being relatively reversible and comprising the presynaptic neurotoxins of Bungarus multicinctus, Family Elapidae, subfamily Elapinae, these neurotoxins collectively being referred to as β-Bungarotoxin. Similar presynaptic neurotoxins include Taipoxin from Oxyuranus scutellatus, Notexin from Notechis scutatus, and Crotoxin from Crotalus durissus terrificus.

The compositions of matter of U.S. Pat. No. 4,341,762 preferably are provided also with a further component comprising a venom having the capability of stimulating the immune mechanism of the body, this stimulation being considered as taught by the patent to include both the cell-mediated immune system and the interferon system, these systems being considered to be simultaneously operative in mammals. Preferred choices according to the aforesaid patent for this third component of the compositions of matter so described include venoms of the Family Viperidae, and particularly the several genera of the subfamily Crotalinae. Due to availability and suitable activity, the aforesaid patent particularly discloses the use of the venom of Agkistrodon piscivorus.

While U.S. Pat. No. 4,341,762 describes the preferred use of the whole venom for the viperid component, the present compositions of matter find particular utility in that the use thereof is accomplished without hemorrhagic effect. In particular, the removal from the viperid venom of enzymes such as L-amino acid oxidase and phosphodiesterase according to the teachings of the present invention is considered advantageous since the viperid venom fraction remaining proves to be sufficiently stimulative of the immune mechanisms and to provide physiologically active compounds which also liberate or stimulate the production of pharmacologically active substances in the body.

SUMMARY OF THE INVENTION

The present invention provides pharmacologically active compositions of matter comprised of snake venoms and/or snake venom fractions administered in disease mitigating quantities into the systemic circulation of mammals, preferably by injection, for the treatment of the symptomology of progressive degenerative neurological disorders including the disease complex generally referred to as arthritis and particularly rheumatoid arthritis. The present compositions of matter are also useful in the treatment of viral and autoimmune disorders by stimulation of the immune mechanisms of the body.

The present compositions of matter are similar to and are used in essentially the same manner as those compositions of matter described in U.S. Pat. No. 4,341,762 to William E. Haast, the inventor of the present compositions of matter. The disclosure of U.S. Pat. No. 4,341,762 is incorporated hereinto by reference.

The present compositions of matter are distinguished from the compositions of matter of U.S. Pat. No. 4,341,762 by the substitution of a particular viperid venom component for the whole venom of the Family Viperidae, subfamily Crotalinae as is disclosed in U.S. Pat. No. 4,341,762. Of particular utility according to the present invention is the "b" fraction of the venom of Agkistrodon piscivorus which is eluted on a G50 column, the "b" fraction being substantially free of enzymes such as L-amino acid oxidase and phosphodiesterase and further in use being characterized by the absence of a hemorrhagic effect when used in the several treatments noted herein and in U.S. Pat. No. 4,341,762.

Accordingly, it is a primary object of the present invention to provide compositions of matter having utility in the treatment of degenerative neurological disorders, viral disorders and autoimmune disorders.

The objects and advantages of the present invention will be understood in light of the present disclosure as well as the disclosure provided in U.S. Pat. No. 4,341,762.

DESCRIPTION OF THE PREFERRED EMBODIMENTS

In U.S. Pat. No. 4,341,762, the viperid venom component of the compositions of matter disclosed and claimed in the patent is preferably utilized as a whole venom due at least in part to the ease of such use. According to the present disclosure, a viperid component of the compositions of matter described in U.S. Pat. No. 4,341,762 is taken to comprise a fraction of a venom of the Family Viperidae, and particularly the several genera of the subfamily Crotalinae. Due to availability and suitable activity, the viperid venom fraction according to the present invention is derived from the venom of Agkistrodon piscivorus.

The viperid component of the present compositions of matter can be prepared from at least one species of the various subfamilies of the Family Viperidae, particularly the subfamilies Viperinae and Crotalinae. The Crotalinae are preferred and particularly include the genera Agkistrodon, Bothrops, Crotalus, Lachesis, Sistrurus and Trimeresurus. The viperid component is particularly intended to function within the present compositions of matter to stimulate in a direct manner the immune systems of the body as well as to stimulate production of pharmacologically active substances such as interferon or precursors thereto. Stimulation of the body's immune systems or mechanisms is seen to have particular significance in the treatment of diseases which are viral or autoimmune in nature, the symptomology of diseases as apparently widely varying as rheumatoid arthritis and multiple sclerosis being treated according to the invention due likely to having generally similar causes. The disorders to which the present compositions of matter apply coincide with those disorders referred to in U.S. Pat. No. 4,341,762.

A preferred protocol for the preparation of the viperid component of the present compositions of matter initially involve the collection of raw venom from a particular species of snake as noted above, raw venom production being by known methodology. As noted above, the venom of Agkistrodon piscivorus is preferred. Venom is collected in all instances from healthy animals of known species origin. After venom collection, the raw liquid venom is centrifuged and lyophilized according to known procedures. The lyophilized venom from serial extractions is pooled into batch lots and stored at $-15°$ C. Once sufficient venom quantities are accumulated, the accumulated quantity is reconstituted in a ratio of 1 gram of lyophilized venom to 5 milliliters of 18 megohm water. The reconstituted venom is then centrifuged at approximately 12,000 rpm $(20,000 \times G)$ at $0°$ C. for 30 minutes. The resulting clear supernatent is withdrawn and frozen prior to lyophilization to produce a dry powder which is stored at $-15°$ C. The lyophilized venom thus produced is designated by species and referred to as raw material of the species. In the event sufficient animals are available for production of a desired quantity of venom, the raw liquid venom, collected cold, can be centrifuged as noted above, frozen and lyophilized to produce a suitable raw material.

Centrifuged and lyophilized venom constituting the raw material for the viperid component of the present compositions of matter is produced according to the procedures noted above. The lyophilized raw material for the viperid component is column fractionated using Sephadex G-50, the buffer being 0.1M sodium acetate, pH 5.2 and containing 0.005 percent Thimerosal. To prepare the column, multiples of 25 grams of Sephadex G-50 Superfine available from Pharmacea, Inc. of Piscataway, N.J. are suspended in multiples of 1 liter units of 18 megohm water and then boiled for two hours. After cooling and settling of the gelled particles, the supernatent is removed by decantation and the Sephadex is washed twice more by resuspension and settling using water. Subsequently, the Sephadex is suspended in buffer and the slurry packed into a Pharmacea K100/100 ($10 \times 100$ cm) chromatography column water-jacketed at $5°$ C. using a Colora recirculating cooler. After packing the column, it is washed with at least two column volumes of the same buffer at a flow rate of 200 ml per hour. A 4.5 gram quantity of the raw material preferably consisting of the lyophilized venom of Agkistrodon piscivorus is dissolved in 22.5 ml of buffer and pumped in ascending direction onto the column at the rate of 7.5 ml per hour. The column is then eluted with buffer at the rate of 2.5 $ml/cm^2/hour$, the effluent being monitored at 280 nm using an LKB 2138 Uvicord S or Uvicord II. Three groups of fractions are eluted from the column, fraction a corresponding to the void volume of the column and containing various enzymatic material; fraction b containing toxic fractions and preceding the low molecular weight peptides of fraction c; and fraction c being the inclusion volume of the column and containing low molecular weight peptides. The fraction b is the preferred viperid component and is substantially absent of enzymatic materials such as L-amino acid oxidase and phosphodiesterase. Fraction b is then placed into an ultra filtration cell (Millipore Number XX42 142 50) equipped with an ultrafiltration filter (Millipore Number PSAC 142 50) having a 1000 nominal molecular weight cutoff with nitrogen pressure on the cell being approximately 50 psi. After volume reduction, approximately 500 ml of 18 megohm water is introduced into the cell and the amount is again volumetrically reduced with the process being repeated and the final retentate being withdrawn from the cell and delivered into clean flasks for freezing. The frozen retentate is then lyophilized by connecting the flask to an automatic freeze drier, Vartis Model No. 10-010 in a known manner. The lyophilized material is designated "viperid bulk powder" and is stored at $-15°$ C.

The viperid component prepared as aforesaid is mixed with bulk powders designated as "Krait bulk powder" and "cobra bulk powder" prepared by processes described in U.S. Pat. No. 4,341,762. While the ratios of the various bulk powders can vary and while the dilution thereof within the solution intended for administration can also vary, a typical mixture is formed by mixture of a first solution comprising 0.88 grams of Thimerosal in 2.0 l of injectible saline. A second solution is prepared using 0.176 g each of the Krait bulk powder and of the cobra bulk powder with the viperid bulk powder being varied in the mixture from 0.176 g to 1.76 g, the bulk powders being mixed in 2.0 l of injectible saline. The first and second solutions are mixed and passed through a prefilter, the prefilter being washed with two 1.0 l washes of injectible saline. Approximately 2.8 l of injectible saline is then added to the resulting solution to produce a quantity of bulk solution sufficient to comprise 8.8 liters. The bulk solution thus produced is passed through a sterile filter and then packaged. Prefiltration and packaging are accomplished according to the disclosure of U.S. Pat. No. 4,341,762.

In use, the dosage of the composition is initiated at approximately 0.10 cc daily, preferably administered subcutaneously in the deltoid region of the upper arm, administration being made to alternate arms. Pharmaceutical administration and patient evaluation is accomplished according to the disclosure of U.S. Pat. No.4,341,762.

Treatment of individuals suffering from the disease syndromes referred to herein is identical to that described in U.S. Pat. No. 4,341,762 relative to the compositions of matter disclosed in said patent. Efficacy and safety of the present compositions of matter have shown to be substantially identical to the compositions of matter disclosed in U.S. Pat. No. 4,341,762.

Tests of the present compositions of matter on rabbits in dosages exceeding on a body weight basis those dosages suggested for use with humans show that the present compositions of matter, even in quantity, exhibit no hemorrhagic effects.

Although it is believed to be apparent from the foregoing, it is also to be understood that the present compositions of matter are useful in the practice of veterinary medicine, such as in the treatment of canine arthritis.

What is claimed is:

1. A composition of matter having pharmacological activity comprising in an administerable form effective amounts of at least one postsynaptic neurotoxin, at least one presynaptic neurotoxin, and a fraction of a viperid venom capable of stimulating the immune mechanisms of the body, the viperid fraction being the b fraction obtained from elution of the viperid venom on a Sephadex G-50 column.

2. The composition of matter of claim 1 wherein the viperid venom comprises a venom of the Family Viperae, subfamily Crotalinae.

3. The composition of matter of claim 2 wherein the viperid venom is the venom of Agkistrodon piscivorus.

4. The composition of matter of claim 1 wherein the viperid fraction excludes the enzymes L-amino acid oxidase and phosphodiesterase.

5. A composition of matter having pharmacological activity and having therapeutic benefits in the treatment of the symptomology of progressive degenerative neurological diseases, the disease complex known as arthritis, viral infections and autoimmune disorders comprising in an administerable form effective amounts of a postsynaptic neurotoxin obtained from the venom of an elapid snake, a presynaptic neurotoxin obtained from the venom of an elapid snake, and a venom fraction stimulative of the immune system obtained from a viperid snake, the fraction being the b fraction obtained from elution of the viperid venom on a Sephadex G-50 column.

6. The composition of claim 5 wherein the viperid venom comprises a venom of the Family Viperae, subfamily Crotalinae.

7. The composition of matter of claim 6 wherein the viperid venom comprises Agkistrodon piscivorus.

8. The composition of matter of claim 5 wherein the fraction excludes the enzymes L-amino acid oxidase and phosphodiesterase.

9. A method of treatment of mammals including man suffering from progressive degenerative neurological disease comprising administering to the mammal a disease mitigating amount of a mixture comprised of at lesat one postsynaptic neurotoxin, at least one presynaptic neurotoxin, and a venom fraction taken from a viperid snake and which is stimulative of the immune mechanism, the fraction being the b fraction obtained from elution of the viperid venom on a Sephadex G-50 column.

10. The method of claim 9 wherein the venom fraction is taken from a viperid snake of the Family Viperae, subfamily Crotalinae.

11. The method of claim 9 wherein the venom fraction is taken from a viperid snake which comprises Agkistrodon piscivorus.

12. The method of claim 9 wherein the venom fraction excludes the enzymes L-amino aicd oxidase and phosphodiesterase.

* * * * *